| United States Patent [19] | [11] | 4,329,325 |
|---|---|---|
| Vollbrecht et al. | [45] | May 11, 1982 |

[54] CYANURIC CHLORIDE MIXTURES AND PROCESS FOR PRODUCING SAME

[75] Inventors: Heinz-Rudiger Vollbrecht, Stein; Fritz Wagner, Munchsmunster, both of Fed. Rep. of Germany

[73] Assignee: SKW Trostberg Aktiengesellschaft, Trostberg, Fed. Rep. of Germany

[21] Appl. No.: 65,021

[22] Filed: Aug. 9, 1979

[30] Foreign Application Priority Data

Sep. 11, 1978 [DE] Fed. Rep. of Germany ....... 2839384

[51] Int. Cl.$^3$ ................................................ C01C 3/08
[52] U.S. Cl. ............................. 423/267; 423/371
[58] Field of Search ............... 423/371, 383, 265, 267, 423/275

[56] References Cited

U.S. PATENT DOCUMENTS 3,269,799  8/1966  Gunn ................................... 423/336
3,661,519  5/1972  Priscoll ............................... 423/336
3,772,427 11/1973  Moore ................................. 423/337

FOREIGN PATENT DOCUMENTS 256409  5/1963  Australia ............................. 423/383
44-31583 12/1969  Japan ................................... 423/383

Primary Examiner—O. R. Vertiz
Assistant Examiner—Wayne A. Langel
Attorney, Agent, or Firm—Thomas L. Tully

[57] ABSTRACT

Process for the production of cyanuric chloride mixtures in which the cyanuric chloride is resistant to agglomeration during storage and handling and is resistant to undesirable hydrolysis, without reducing the reactivity of the cyanuric chloride with respect to organic reactants. The present mixtures contain cyanuric chloride and a minor amount by weight of a finely divided, inert, hydrophobic filler material to form a new, homogeneous, particulate cyanuric chloride composition in which the cyanuric chloride particles are surrounded by the inert filler particles.

13 Claims, No Drawings

# CYANURIC CHLORIDE MIXTURES AND PROCESS FOR PRODUCING SAME

BACKGROUND OF THE INVENTION

Cyanuric chloride is a known chemical having a variety of known applications. Also a number of useful derivatives of cyanuric chloride can be made by the successive substitution of one, two, or all three chlorine atoms of the cyanuric chloride. The synthesized derivatives are used for the production of herbicides, optical brighteners, or vulcanization promoters, for example. Generally, the cyanuric chloride is added in solid form to organic solvents or water to produce a solution or suspension and is then reacted to form the desired derivative.

When cyanuric chloride is added to very cold aqueous solutions or suspensions, it is desirable to have the cyanuric chloride react as rapidly as possible, since cyanuric chloride, being an acid chloride, reacts with water to produce undesirable cyanuric acid and hydrochloric acid.

In the past, rapid reaction has been accomplished by preceding the dissolution and/or suspension of cyanuric chloride in water by mechanical crushing (e.g. grinding) of the cyanuric chloride. However, this method has significant disadvantages, due to the danger of corrosion of the moving mechanical parts of the crushing apparatus caused by the cyanuric chloride. There is also the danger that the resultant corrosion product will enter the reaction solution and will contaminate and/or spoil the end product being produced.

One known process for solving this problem consists in spraying liquid molten cyanuric chloride (melting point 146° C.) into the corresponding solvent (German Offenlegungsschrift No. 24,54,910). The cyanuric chloride particles produced during the quenching process are for the most part sufficiently fine to allow a rapid reaction between the cyanuric chloride and the corresponding reactants. However, shipping, storage, and in-plant handling of cyanuric chloride at temperatures above 146° C. pose considerable technical problems and involve high cost. Since cyanuric chloride, like all chlorides, is a corrosive medium, its handling is not without danger, especially in view of the high temperature.

SUMMARY OF THE INVENTION

The principal object of the present invention is to produce cyanuric chloride in a stable finely divided form suitable for reaction in an aqueous solution or suspension, which does not have the known disadvantages.

This is achieved according to the present invention by mixing a minor amount by weight, up to about 10% by weight, of an inert, finely-divided, hydrophobic filler material with cyanuric chloride to form a homogeneous, finely-divided cyanuric chloride composition comprising a mixture of the cyanuric chloride particles surrounded by the inert filler particles, the latter forming a protective surface coating which reduces the tendency of the cyanuric chloride particles to agglomerate into larger particles or lumps without reducing the reactivity of the cyanuric chloride particles in an aqueous solution or suspension with respect to organic reactants.

Preferably, the cyanuric chloride is mixed in gaseous form with the inert filler so that the cyanuric chloride solidifies in special form in the presence of the filler particles.

In the cyanuric chloride mixtures of the present invention, the particulate hydrophobic filler surrounds the fine cyanuric chloride particles and thereby counteracts any undesirable hydrolysis, while at the same time not interfering with its reactivity with organic reactants. In addition, the primary cyanuric chloride particles, which are initially formed during the production of the mixture, are protected by the filler particles so that secondary agglomerates or particle clusters or lumps, which otherwise generally form in particulate cyanuric chloride compositions, are inhibited. Therefore, the cyanuric chloride mixtures produced according to the invention have an excellent flow behavior.

Fillers suitable for use according to the present invention include substantially any hydrophobic material which does not react with cyanuric chloride, i.e., which is inert with respect to cyanuric chloride and its reaction partners and reaction products. Both inorganic and organic fillers may be used. The fillers may have inherent hydrophobic properties or they can be treated to produce such properties, such as by treating silanes, and the like, to make them hydrophobic. Hydrophobic fumed or precipitated silica, hydrophobic aluminum oxide, hydrophobic aluminum silicates, hydrophobic calcium silicate and mixtures thereof are especially preferred. The fillers used should advantageously be as finely-divided or powdered as possible and should have a large specific surface, at least 60 $m^2/g$.

The hydrophobic filler content is preferably from about 0.1 to 3 weight percent, most preferably from about 0.2 to 0.7 weight percent.

The cyanuric chloride mixtures of the present invention are produced by the intensive mixing of the hydrophobic filler particles with the untreated or pure cyanuric chloride. Preferably, admixture proceeds as long as primary or pure cyanuric chloride particles are present. This is the case with gaseous cyanuric chloride prior to its desublimation or immediately after desublimation. Therefore, preferably manufacture of the present mixtures takes place during the initial production of cyanuric chloride as the final production step in the process.

DESCRIPTION OF PREFERRED EMBODIMENTS

Hydrophobic fumed silica is added at the rate of 1.0 kg/h to a gas stream of cyanuric chloride vapor (200 kg/h) and air (150 kg/h) immediately before the vapor enters a condenser at 180° C.

As soon as the cyanuric chloride changes from a gas to a solid, the cyanuric chloride particles become coated with the hydrophobic fumed silica. In addition, the formed coating particles are mixed in a mixer for homogenization. When the resultant special cyanuric chloride mixture is added to an aqueous solution or suspension for atrazine synthesis, without mechanical crushing of the product, atrazine contents of 96% or more can be achieved.

If atrazine synthesis is carried out in the same way but using cyanuric chloride, which has not been mixed with hydrophobic silica and mechanically crushed, atrazine contents of only 90 to 92% result.

Variations and modifications will be apparent to those skilled in the art in the light of the present disclosure and within the scope of the present claims.

We claim:

1. Particulate cyanuric chloride mixture which is resistant to agglomeration during storage and handling and is resistant to undesirable hydrolysis comprising finely-divided particles of cyanuric chloride and from about 0.1% up to about 10% by weight, of at least one hydrophobic filler having a specific surface of at least 60 m$^2$/g., said filler being inert with respect to said cyanuric chloride.

2. Cyanuric chloride mixture according to claim 1 which contains from about 0.1 to 3% by weight of the hydrophobic filler.

3. Cyanuric chloride mixture according to claim 1 which contains from about 0.2 to 0.7% by weight of the hydrophobic filler.

4. Cyanuric chloride mixture according to claim 1 in which said hydrophobic filler is selected from the group consisting of silica, aluminum oxide, aluminum silicate, calcium silicate, and mixtures thereof.

5. Cyanuric chloride mixture according to claim 1, 2, or 3 in which filler comprises hydrophobic fumed silica.

6. Cyanuric chloride mixture according to claim 1, 2 or 3 characterized by cyanuric chloride particles which are coated with the hydrophobic filler.

7. Process for producing cyanuric chloride which is resistant to agglomeration during storage and handling and is resistant to undesirable hydrolysis, comprising mixing cyanuric chloride with from about 0.1% up to about 10% by weight of at least one finely-divided hydrophobic filler having a specific surface of at least 60 m$^2$/g., said filler being inert with respect to said cyanuric chloride.

8. Process according to claim 7 in which said hydrophobic filler is mixed with said cyanuric chloride in an amount of from about 0.1 to 3% by weight.

9. Process according to claim 7 in which said hydrophobic filler is mixed with said cyanuric chloride in an amount of from about 0.2 to 0.7% by weight.

10. Process according to claim 7 in which said hydrophobic filler is selected from the group consisting of silica, aluminum oxide, aluminum silicate, calcium silicate and mixtures thereof.

11. Process according to claim 7, 8 or 9 in which said filler comprises hydrophobic fumed silica.

12. Process according to claim 7, 8, 9 or 10 in which said hydrophobic filler is added and mixed with said cyanuric chloride while said cyanuric chloride is in the gaseous state and said cyanuric chloride is changed to the solid state in the presence of said filler.

13. Process according to claim 7, 8, 9 or 10 in which said cyanuric chloride is condensed from the gaseous state to the solid state and the hydrophobic filler is homogeneously mixed with said solid particulate cyanuric chloride immediately after the condensation.

* * * * *